(12) United States Patent
Feussner et al.

(10) Patent No.: US 7,321,025 B2
(45) Date of Patent: Jan. 22, 2008

(54) ISOLATED OXIDE SYNTHASE AND DIVINYL ETHER SYNTHASE AND USES THEREOF

(75) Inventors: Ivo Feussner, Göttingen (DE); Michael Stumpe, Fribourg (CH)

(73) Assignee: BASF Plant Science GmbH (DE)

( * ) Notice: Subject to any disclaimer, the term of this patent is extended or adjusted under 35 U.S.C. 154(b) by 223 days.

(21) Appl. No.: 10/483,328

(22) PCT Filed: Jul. 6, 2002

(86) PCT No.: PCT/EP02/07555

§ 371 (c)(1),
(2), (4) Date: Jul. 13, 2004

(87) PCT Pub. No.: WO03/006647

PCT Pub. Date: Jan. 23, 2003

(65) Prior Publication Data

US 2005/0223437 A1    Oct. 6, 2005

(30) Foreign Application Priority Data

Jul. 12, 2001  (DE) ............... 101 33 343
May 6, 2002    (DE) ............... 102 20 115

(51) Int. Cl.
*A01H 5/00*   (2006.01)
*C12N 15/29*  (2006.01)
*C12N 15/82*  (2006.01)

(52) U.S. Cl. ............... 530/370; 530/350; 435/419; 435/69.1

(58) Field of Classification Search ............... 530/350
See application file for complete search history.

(56) References Cited

FOREIGN PATENT DOCUMENTS

WO    WO 01/38484 A2    5/2001
WO    WO 02/29018 A2    4/2002

OTHER PUBLICATIONS

W. Song, et al., "Molecular Cloning of an Allene Oxide Synthase: A Cytochrome P450 Specialized for the Metabolism of Fatty Acid Hydroperoxides," *Proc. Natl. Acad. Sci. USA*, vol. 90, pp. 3519-8423, Sep. 1993.
K. Harms, et al., "Expression of a Flax Allene Oxide Synthase cDNA Leads to Increased Endogenous Jasmonic Acid (JA) Levels in Transgenic Potato Plants but Not to a Corresponding Activation of JA-Responding Genes," *The Plant Cell*, vol. 7, pp. 1645-1654, Oct. 1995.
C. Wang, et al., "Overexpression of a Cytoplasm-Localized Allene Oxide Synthase Promotes the Wound-Induced Accumulation of Jasmonic Acid in Transgenic Tobacco," *Plant Molecular Biology*, vol. 40, pp. 783-793, 1999.
Z. Pan, et al., "The Major Protein of Guayule Rubber Particles is a Cytochrome P450: Characterization Based on cDNA Cloning and Spectroscopic Analysis of the Solubilized Enzyme and Its Reaction Products," *The Journal of Biological Chemistry*, vol. 270, No. 15, pp. 8487-8494, 1995.
GenBank accession No. AJ271093, created Apr. 16, 2000.
H. Maucher, et al., "Allene Oxide Synthases of Barley (*Hordeum Vulgare cv. Salome*): Tissue Specific Regulation in Seedling Development," *The Plant Journal*, vol. 21, No. 2, pp. 199-213, 2000.
A. Itoh, et al., "Molecular Cloning of a Divinyl Ether Synthase: Identification as a CYP74 Cytochrome P-450," *The Journal of Biological Chemistry*, vol. 276, No. 5, pp. 3620-3267, 2000.
GenBank accession No. AJ309541, created Feb. 3, 2001.
M. Stumpe, et al., "A Pathogen-Inducible Divinyl Ether Synthase (CYP74D) from Elicitor-Treated Potato Suspension Cells," *FEBS Letters*, vol. 507, pp. 371-376, 2001.
T. K. Zank, et al., "Cloning and Functional Expression of the First Plant Fatty Acid Elongase Specific for $\Delta^6$-Polyunsaturated Fatty Acids," *Biochemical SocietyTransactions*, vol. 28, Part 6, pp. 654-658, 2000.
T. Girke, et al., "Identification of a Novel $\Delta6$-Acyl-Group Desaturase by Targeted Gene Disruption in Physcomitrella Patens," *The Plant Journal*, vol. 15, No. 1, pp. 39-48, 1998.

*Primary Examiner*—Medina A. Ibrahim
(74) *Attorney, Agent, or Firm*—Connolly Bove Lodge & Hutz LLP

(57) ABSTRACT

The present invention relates to enzymes from the cytochrome P450 family and to the nucleotide sequences encoding them, and to their use in a method for the generation of pathogen-resistant plants.

16 Claims, 9 Drawing Sheets

ISOLATED OXIDE SYNTHASE AND DIVINYL ETHER SYNTHASE AND USES THEREOF

RELATED APPLICATIONS

This application is a national stage application (under 35 U.S.C. 371) of PCT/EP02/07555 filed Jul. 6, 2002, which claims the benefit of German application 10133343.9 filed Jul. 12, 2001 and of German application 10220115.3 filed May 6, 2002.

FIELD OF THE INVENTION

The present invention relates to enzymes from the cytochrome P450 class, to the isolation of the corresponding coding nucleotide sequences and to their use in a method for generating pathogen-resistant plant cells and their progeny.

BACKGROUND OF THE INVENTION

The cytochrome P450 enzyme class includes the enzymes allene oxide synthase (AOS), hydroperoxide lyase (HPL) and divinyl ether synthase (DES). They form a separate subfamily referred to as CYP74.

Owing to the multiplicity of cytochrome P450 enzymes, a nomenclature was developed which assigns a specific family and subfamily to each protein of this class on the basis of its primary structure. Thus, all the AOSs form their own subfamily CYP74A, while CYP74B comprises the 13-HPLs, CYP74C the 9/13-HPLs and CYP74D the 9-DESs (Feussner et al.; 2001, *Trends Plant Sci.* 6, 268-273). Proteins from the same subfamily are numbered chronologically.

CYP74 enzymes are monooxygenases with a hemamolecule of prosthetic group. Although they also have a protoporphyrin IX group (hem b) attached as prosthetic group, they have very little affinity to CO (Matsui, 1998, *Belgian Journal of Botany.* 131, 50-62).

They constitute important enzymes in the metabolism of polyene fatty acids, which is known as the lipoxygenase (LOX) pathway (Feussner and Wasternack, 1998, *Fett/Lipid.* 100, 146-152).

LOXs are dioxygenases in which the iron in the catalytic center is bound to amino acid side chains (Brash, 1999, *J. Biol. Chem.* 274, 23679-23682). They catalyze the incorporation of molecular oxygen into the (1Z,4Z)-pentadiene system of polyunsaturated fatty acids. In plants, these are mainly linoleic and α-linolenic acid. Depending on the regioselectivity of the LOX employed, two different positional isomers of hydroperoxides, viz. (9S) isomers or (13S) isomers, may arise as products. For example, α-linolenic acid gives rise to (13S,9Z,11E,15Z)-13-hydroperoxy-9,11,15-octadecatrienoic acid (13S-HPOTE) and linoleic acid gives rise to (13S,9Z,11E)-13-hydroperoxy-9,11-octadecadienoic acid (13S-HPODE).

In plants, these hydroperoxides are rapidly reacted further by a multiplicity of enzymes. Currently, seven different enzyme families which convert hydroperoxides and thus compete for LOX products are known in the plant kingdom: the allene oxide synthase (AOS) reaction, the hydroperoxide lyase (HPL) reaction, the divinyl ether synthase (DES) reaction, the reductase reaction, the peroxygenase reaction, the epoxyalcohol synthase (EAS) reaction and the LOX reaction itself (Feussner et al.; 2001, *Trends Plant Sci.* 6, 268-273). When 13-HPOTE is reacted in the presence of the enzyme allene oxide cyclase (AOC), a cyclization reaction takes place which gives 12-oxophytodienoic acid (12-oxo-PDA) (Ziegler et al.; 2000, *J. Biol. Chem.* 275, 19132-8), which, in turn, is the precursor of jasmonic acid, which is here considered a plant hormone.

AOS (EC4.2.1.92; CYP74A) was the first CYP74 enzyme to be described; the homogeneous protein was first isolated from flax (Song and Brash, 1991, *Science.* 253, 781-784). It catalyzes the reaction which gives an unstable allene oxide which can break down into the corresponding α- and γ-ketoles in the presence of water. AOS is involved in the biosynthesis of jasmonic acid (Vick and Zimmerman, 1983, *Biochem. Biophys. Res. Commun.* 111, 470-7). Jasmonic acid itself is involved in inducing the transcription of specific mRNA and regulating the translation of jasmonate-induced proteins (JIP), such as LOX, AOS and proteinase inhibitors. This makes jasmonic acid an important signal substance in plant stress response (Wasternack and Parthier, 1997, *Trends Plant Sci.* 2, 302-307). An involvement in processes of growth regulation and in the promotion of senescence is likewise described (Sembdner and Parthier, 1993, *Annu. Rev. Plant Physiol. Plant Mol. Biol.* 44, 569-589).

A large number of AOSs have already been cloned and expressed functionally in *E. coli*, including the *Arabidopsis thaliana, Lycopersicon esculentum, Linum usitatissimum* and *Hordeum vulgare* AOSs. Apart from the barley AOSs, all of the AOSs cloned to date show substrate specificity for (13S)-hydroperoxide (Maucher et al.; 2000, *Plant J.* 21, 199-213).

HPL (CYP74B and C) cleaves the hydroperoxide into (3Z)-aldehydes and ω-oxoacids (Matsui, 1998, *Belgian Journal of Botany.* 131, 50-62). Even before the enzyme itself was discovered, the HPL reaction products were known as "leaf aldehydes", which contribute to the characteristic odor of plants and fruits (Hatanaka, 1996, *Food Rev. Int.* 12, 303-350). In the case of 13-HPOTE as substrate, (3Z)-hexenal and (9Z)-12-oxo-9-dodecenoic acid are formed, the latter of which isomerizes to give (10E)-12-oxo-10-dodecenoic acid (traumatin), which is discussed as a wound hormone. A function as plant messenger substance is also discussed (Bate and Rothstein, 1998, *Plant J.* 16, 561-569). Traumatin can be oxidized further to give traumatic acid, which likewise appears to be involved in plant wound response (Zimmerman and Vick, 1970, *Plant Physiol.* 46, 445-453). HPLs which were cloned and expressed in *E. coli* as active protein were the *A. thaliana, Cucumis sativus, Medicago sativus* and *L. esculentum* HPLs, inter alia. Again, most of these enzymes show substrate specificity for (13S)-hydroperoxide. Only one HPL from cucumber and one from melon are without substrate specificity and are therefore referred to as 9/13-HPL (McIntyre et al.; 1999, *J. Biol. Chem.* 274, 25189-25192; Matsui et al.; 2000, *FEBS Lett.* 481, 183-188). A study of the relationship of both sequences with other members of the CYP74 family reveals a higher degree of homology with AOS than with the 13-HPLs. This is why these enzymes are classified as a separate subfamily CYP74C (Matsui et al.; 2000, *FEBS Lett.* 481, 183-188). It has been demonstrated that the *Arabidopsis* HPL is induced by wounding.

DES (CYP74D) catalyzes the formation of divinyl ethers which are fungicidally active (Weber et al. 1999). An involvement of the divinyl ethers in the defense against pathogenic fungi and bacteria, analogously to the aldehydes in the case of the HPL products, is also discussed (Weber et al.; 1999, *Plant Cell.* 11, 485-493; Göbel et al.; 2001, *J. Biol. Chem.* 276, 6267-6273). The first *L. esculentum* DES was cloned in 2001 by Itoh and Howe. It emerged that it has a high degree of homology on a sequence with AOS and HPL; it is therefore also thought as belonging to the cytochrome P450 class, subfamily CYP74D. Moreover, DES is unique in the CYP74 group in as far as it is the only enzyme which is highly specific for 9S-hydroperoxide (Itoh and Howe, 2001, *J. Biol. Chem.* 276, 3620-3627).

In nature, P450 enzymes are involved in many ways in the biosynthesis and the metabolism of a large number of endogenous substances. Their involvement in the detoxification of xenobiotics is of particular importance. Moreover, plant P450 enzymes are involved in the biosynthesis of wound signals (jasmonic acid, salicylic acid, traumatin) and hormones (gibberellins, brassinosteroids).

Substances which trigger wound signals in plants and subsequent signal transduction cascades come in many forms. They can be triggered by damage or injury to the plant, but can also be induced (artificially) by external chemical compounds.

In addition, however, it is in particular the incidence of plant diseases and mainly the promotion of plant's defense reactions against such pathogens which are agronomically of enormous relevance. The plant's response to a pathogen may involve quite a different pathway than is the case when the plant defends itself against stress by wounding. The incidence of plant diseases caused by, for example, viruses, bacteria or fungi, generally results in considerable damage or indeed death of the whole plant, in conjunction with a drastic quantitative or qualitative reduction of the crop.

If the yield losses are to be limited to an economically acceptable extent, it is imperative to carry out plant protection measures. In particular, it would be desirable to improve the plants' defense reactions against pathogens and/or pests without using chemicals, which constitute an additional pollutant for the soil, the groundwater and the user.

SUMMARY OF THE INVENTION

An object of the present invention was therefore to provide transgenic plant cells, plants and their progeny which display increased resistance to pathogens, and correspondingly improved methods for their generation.

This object is achieved by an allene oxide synthase with an amino acid sequence as shown in SEQ ID No. 2 or its isoenzymes and/or a divinylether synthase with an amino acid sequence as shown in SEQ ID No. 4 or its isoenzymes.

The two abovementioned enzymes belong to the CYP74 enzyme family. An increased specific activity of these CYP74 enzymes, alone or in combination, with regard to the endogenous specific activity of these enzymes in a plant cell leads to an increased resistance to pathogens in a plant cell.

Here, the specific CYP enzyme activity which is increased in accordance with the invention brings about a resistance of the plant cells or plants to pathogens which is increased by 20-90%, preferably by 30-80% and especially preferably by 40-70% over the specific endogenous activity in plant cells or plants. The resistance of the plants is determined by a drop in penetration frequency.

For the purpose of the invention, penetration frequency is understood as meaning the number of infection sites with successfully penetrated epidermal cell, divided by the total number of infection sites.

DESCRIPTION OF THE INVENTION

Figure 1:
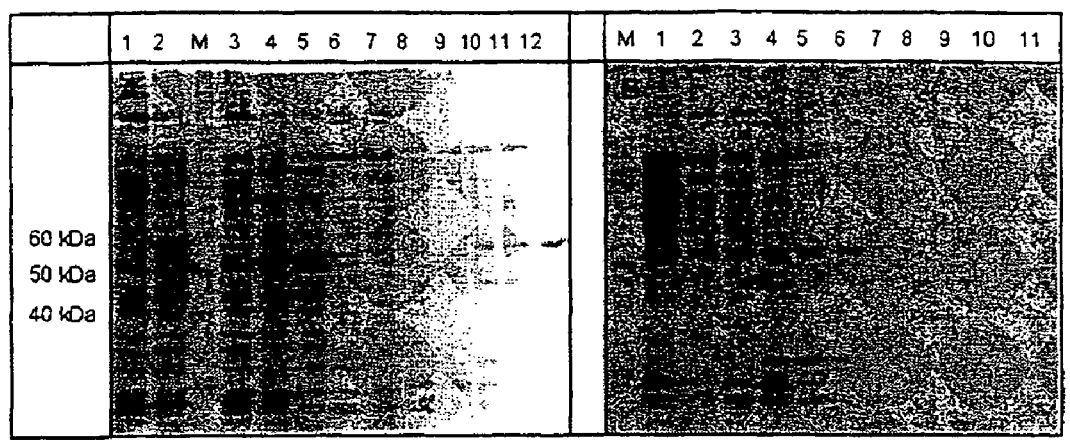
FIG. 1. Affinity purification of clone Pp291: (A) Elution with pH gradient, and (B) elution gradient with imidazole gradient.

The CYP74 enzymes according to the invention, alone or in combination, advantageously bring about an increased resistance in plants to pathogens such as, for example, biotrophy fungi. An increased concentration (increased specific activity) in CYP74 protein(s) according to the invention preferably brings about increased resistance to powdery mildews, especially preferably *Blumeria graminis* f. sp. *hordei* or f. sp. *tritici*. However, this does not preclude an increased resistance to other plant pathogens.

Further examples of such plant pathogens are *Pythium* spec., *Albugo* spec., *Rhizoctonia solani*, *Peronospora parasitica*, *Erysiphe crucifearum*, *E. cichoreacearum*, *Alternaria brassicicola*, *Botrytis cinerea*, *Sclerotium rolfsii*, *Sclerotinia sclerotium*, *Fusarium oxysporum*, *F. culmorum*, *F. graminearum*, *F. nivale*, *phytophtora infestans* or *Pseudomonas syringae*.

It must be noted that the abovementioned CYP74 enzymes according to the invention display a much broader substrate spectrum than previously known CYP enzymes from this class. The CYP74 enzymes according to the invention are capable of converting not only 9-HPOD/TE, but also 13-HPOD/TE as substrate.

In accordance with the invention, the present CYP74 enzymes originate from moss or higher plants. Preferably, the CYP74 enzymes according to the invention originate from *Physcomitrella patens*.

The present invention also relates to an isolated nucleotide sequence encoding an allene oxide synthase of the abovementioned type which is involved in the biosynthesis of polyunsaturated fatty acids for increasing the resistance of plant cells or plants to pathogens, selected amongst a) a nucleotide sequence as shown in SEQ ID No. 1,
b) a nucleotide sequence with at least 70% identity with the nucleotide sequence shown in SEQ ID No. 1,
c) a nucleotide sequence which is complementary to a) or b).

The invention also encompasses nucleotide sequences which hybridize with a) or b).

Likewise, the invention encompasses an isolated nucleotide sequence encoding a divinyl ether synthase of the abovementioned type which is involved in the biosynthesis of polyunsaturated fatty acids for increasing the resistance of plant cells or plants to pathogens, selected amongst a) a nucleotide sequence as shown in SEQ ID No. 3,
b) a nucleotide sequence with at least 70% identity with a nucleotide sequence shown in SEQ ID No. 3,
c) a nucleotide sequence which is complementary to a) or b).

The invention also encompasses nucleotide sequences which hybridize with a) or b).

In accordance with the invention, an isolated nucleic acid or an isolated nucleic acid fragment is understood as meaning an RNA or DNA polymer which can be single-stranded or double-stranded and which can optionally comprise natural, chemically synthetized, modified or artificial nucleotides. In this context, the term DNA polymer also includes genomic DNA, cDNA or mixtures of these.

Hybridizing nucleotide sequences for the purpose of the invention are understood as meaning oligo- or polynucleotides which bind under standard hybridization conditions with the corresponding nucleotide sequence according to the invention which encodes CYP74 enzymes. The term standard hybridization conditions is to be understood in the broad sense and refers to stringent and less stringent hybridization conditions. Such conditions are described, inter alia, by Sambrook et al. (1989, Molecular Cloning, $2^{nd}$ edition, Cold Spring Harbor Laboratory Press). In accordance with the invention, the term hybridizing sequences includes substantially similar nucleotide sequences from the DNA or RNA group which undergo a specific interaction (binding) with the nucleotide sequences according to the invention under standard hybridization conditions known per se. These also include short nucleotide sequences with a length of, for example, 10 to 30, preferably 12 to 15, nucleotides. In accordance with the invention, this also encompasses what are known as primers or probes, inter alia.

In accordance with the invention, complementary nucleotide sequences are understood as meaning DNA or RNA (mRNA) sequences which constitutes a transcription of the starting sequence in question in accordance with the base pairing rules.

In accordance with the invention, allenes are understood as being functionally equivalent nucleotide sequences, i.e. nucleotide sequences with essentially the same type of action. Functional equivalent sequences are those sequences which retain the desired functions despite a deviating nucleotide sequence, for example owing to the degeneracy of the genetic code. Thus, functional equivalents encompass naturally occurring variants of the sequences described herein as well as artificial nucleotide sequences, for example nucleotide sequences which have been obtained by chemical synthesis and, if appropriate, adapted to the codon usage of the host organism. In addition, functionally equivalent sequences encompass those with a modified nucleotide sequence which impart for example a desensitivity or resistance to inhibitors to the protein.

A functional equivalent is in particular also understood as meaning natural or artificial mutations of an originally isolated sequence which retain the desired function. Mutations encompass substitutions, additions, deletions, exchanges or insertions of one or more nucleotide residues.

Also included here are what are known as sense mutations which at the protein level may, for example, lead to the substitution of conserved amino acids, but which do not lead to a fundamental change in functionality of the protein, i.e. which are functionally neutral. This also includes modifications of the nucleotide sequence which, at the protein level, relate to the N or C terminus of a protein without, however, adversely affecting the function of the protein to a substantial degree. Indeed, these modifications can have a stabilizing influence on the protein structure. Functional equivalents are also those variants whose activity is weakened or enhanced in comparison with the original gene or gene fragment.

Artificial DNA sequences are also subject matter of the present invention, as long as they confer the desired properties, as described above. Such artificial DNA sequences can be determined for example by back translating proteins generated by means of molecular modeling, or by in-vitro selection. DNA sequences which are especially suitable are coding DNA sequences which have been obtained by back translating a polypeptide sequence in accordance with the host-organism-specific codon usage. The specific codon usage can be determined readily by the skilled worker who is familiar with molecular-genetic methods by means of computer evaluations of other, known genes of the organism to be transformed.

The term "functional equivalent" also refers to the protein encoded by the nucleotide sequence in question. In this case, the term "functional equivalent" describes a protein whose amino acid sequence shows a certain percentage of homology with that of the reference protein (in this case the CYP74 enzymes). This percentage is at least 75%, preferably 80%, especially preferably 90-95% and in particular 99.9%.

Furthermore, the present invention also encompasses for example those nucleotide sequences which are obtained by modifying the nucleotide sequence, which results in corresponding derivatives. The aim of such a modification can be for example the further delimitation of the coding sequence present therein or else for example the insertion of further restriction enzyme cleavage sites.

The nucleotide sequences according to the invention are furthermore distinguished by the fact that they originates from moss or higher plants. Preferably, they originate from *Physcomitrella patens*.

By way of clarification of the terminology, it should be pointed out that the protein encoded by SEQ ID No. 1 is a class CYP74A cytochrome P450 enzyme (allene oxide synthase; AOS). Owing to its substrate specificity, inter alia, the enzyme encoded by SEQ ID No. 3 is assigned to the CYP74E class (divinyl ether synthase; DES).

The present invention furthermore relates to a gene construct comprising a nucleotide sequence as shown in SEQ ID No. 1 and/or a nucleotide sequence as shown in SEQ ID No. 3 and regulatory nucleotide sequences which are operatively linked thereto.

The gene constructs according to the invention also include those comprising derivatives, alleles or parts of the nucleotide sequence as shown in SEQ ID No. 1 and/or SEQ ID No. 3. In this context, the coding regions, alone or in combination (i.e. jointly), are under the control of the same regulatory sequences or of a plurality of separate regulatory sequences.

Operative linkage is understood as meaning the sequential arrangement of, for example, promoter, coding sequence, terminator and, if appropriate, further regulatory elements in such a way that each of the regulatory elements can fulfill its intended function when the coding sequence is expressed. These regulatory nucleotide sequences can be of natural origin or be obtained by chemical synthesis. A suitable promoter is, in principle, any promoter which is capable of regulating the gene expression in the host organism in question. According to the invention, such a promoter may also take the form of a natural or synthetically generated chemically inducible promoter by which the expression of the genes governed by it can be controlled in the host cell at a specific point in time. These also include tissue-specific promoters. A gene structure is generated by fusing a suitable promoter to at least one nucleotide sequence according to the invention employing customary recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989). In order to connect the DNA fragments with one another, adapters or linkers may be added to the fragments.

Also encompassed in accordance with the invention are the sequence regions which precede the coding regions (structural genes; 5' or upstream sequence regions) and/or which follow them (3' or downstream sequence regions). Also included are, in particular, sequence regions which have a regulatory function. They are capable of influencing transcription, RNA stability or RNA processing, and translation. Examples of regulatory sequences are, inter alia, promoters, enhancers, operators, terminators or translation enhancers.

Also encompassed by the present invention is a vector comprising an isolated nucleotide sequence as shown in SEQ ID No. 1, alleles, derivatives or parts thereof and/or an isolated nucleotide sequence as shown in SEQ ID No. 3, alleles, derivatives or parts thereof and/or a gene construct of the abovementioned type, and additional nucleotide sequences for selection and/or replication in a host cell and/or for integration into the genome of a host cell.

In general, host cells which are suitable in accordance with the invention can be cells of higher plants. Preferred cells are cells of useful plants, preferably monocotyledoneous useful plants, especially preferably cereals and in particular barley and/or wheat. Preferred cells of dicotyledoneous useful plants are those from the Solanaceae family.

Thus, the present invention also encompasses at least one transgenic plant cell, intact plant and/or their progeny, comprising, in replicable form, an isolated nucleotide sequence as shown in SEQ ID No. 1, alleles, derivatives or parts thereof and/or an isolated nucleotide sequence as shown in SEQ ID No. 3, alleles, derivatives or parts thereof and/or a gene construct of the abovementioned type and/or a vector of the abovementioned type, the transgenic plant cell, intact plant and/or their progeny showing enhanced expression of the nucleotide sequence encoding an allene oxide synthase and/or of the nucleotide sequence encoding a divinyl ether synthase in comparison with the endogenous gene expression (i.e. the natural gene expression as is found, for example, in an untransformed plant or plant cell), which brings about an increased resistance of plants to pathogens.

The reason for enhanced gene expression may be an increased copy number of the nucleotide sequence in question. Alternatively, it is based for example on the fact that the coding region of a nucleotide sequence is linked operatively to one or more regulatory sequences which bring about an enhanced initiation of gene expression. This can be brought about for example by a strong and/or inducible promoter and/or enhancer and/or other regulatory sequences.

As regards the copy number, one or both of the abovementioned nucleotide sequences may be present as 2-100, preferably 5-50 and especially preferably 2-15 copies in a variant of the present invention.

In the abovementioned transgenic plant cells, plants and/or their progeny according to the invention, the nucleotide sequences according to the invention (alone or in combination), alleles, derivatives or parts thereof and/or gene constructs and/or vectors of the abovementioned type may be present extrachromosomally and/or integrated stably into the plant genome.

Suitable procedures and aids, such as gene constructs or vectors, and suitable helper organisms for integrating the nucleotide sequence into the plant genome are known to the skilled worker and will not be detailed further.

The transgenic plant cell, intact plant and/or their progeny which has an allene oxide synthase as shown in SEQ ID No. 2 and/or a divinyl ether synthase as shown in SEQ ID No. 4 and/or corresponding isoenzymes, derivatives and/or parts thereof, the relevant specific activity of the enzymes in the transgenic host systems being increased in comparison with the relevant endogenous enzyme activity (for example in the wild-type cells), is likewise encompassed by the present invention.

Isoenzymes are understood as meaning enzymes with the same or a similar substrate specificity and specificity of action, but with a different primary structure.

In accordance with the invention, derivatives are understood as meaning enzymes with modifications in the sequence, for example at the N and/or C terminus of the polypeptide, or in the conserved amino acid region, without, however, adversely affecting the function of the enzyme. These modifications can be carried out in the form of amino acid substitutions by methods known per se.

A particular embodiment of the present invention encompasses variants of the enzymes according to the invention whose activity, in comparison with the starting protein in question, is reduced or increased owing to amino acid substitutions. The same applies to the stability of the enzymes according to the invention in those cells which are more or less sensitive to, for example, degradation by proteases.

Furthermore, the present invention relates to enzymes with the function of an allene oxide synthase or divinyl ether synthase whose amino acid sequence has been modified in such a way that they are desensitive to regulatory compounds, for example the catabolites which regulate their activity (feedback desensitive).

In accordance with the invention, the abovementioned transgenic plant cell, intact plant and/or their progeny takes the form of a useful plant or its cells, preferably from the Solanaceae family or the cereal family, especially preferably potato, barley or wheat.

The present invention also encompasses a method for increasing the resistance of plant cells or plants to pathogens, wherein a nucleotide sequence as shown in SEQ ID No. 1 and/or a nucleotide sequence as shown in SEQ ID No. 3 and/or a gene construct and/or a vector of the above-detailed type is transferred, in replicable form, into plant cells and intact plants are regenerated from the plant cells thus transformed.

Methods for the generation of such transgenic plants according to the invention are standard laboratory practice. In an advantageous variant of the present invention, the nucleotide sequence and/or gene construct and/or vectors are transferred into the plant or plant parts or cells by what is known as "particle bombardment" and/or by *agrobacteria*-mediated transformation.

A particular advantage of the transgenic plant and its progeny obtained in accordance with the invention is that an increased copy number of at least one of the nucleotide sequences according to the invention or, analogously, the presence of an increased concentration of at least one correspondingly encoded protein, leads to a substantially increased disease resistance. This means that the gene(s) according to the invention and/or the encoded protein(s) is/are causative for the development of the resistance to pathogenic pests. Examples of pathogenic pests are, inter alia, *Blumeria graminis* f. sp. *hordei* or f. sp. *tritici, Pythium* spec., *Albugo* spec., *Rhizoctonia solani, Peronospora para-* sitica, *Erysiphe cruciferarum*, *E. cichoracearum*, *Alternaria brassicicola*, *Botrytis cinerea*, *Sclerotium rolfsii*, *Sclerotinia sclerotium*, *Fusarium oxysporum*, *F. culmorum*, *F. graminearum*, *F. nivale*, *phytophtora infestans* or *Pseudomonas syringae*.

In a preferred variant of the method according to the invention, the plant cells employed are cells of useful plants, preferably from the Solanaceae family or the cereal family, especially preferably potato, barley or wheat.

The present invention furthermore relates to the use of a nucleotide sequence as shown in SEQ ID No. 1 and/or a nucleotide sequence as shown in SEQ ID No. 3 and/or their alleles, derivatives and/or parts thereof for increasing the resistance of transgenic plant cells, intact plants and/or their progeny to pathogens.

The present invention also relates to the use of at least one polypeptide as shown in SEQ ID No. 2 and/or a polypeptide as shown in SEQ ID No. 3 and/or isoenzymes and/or derivatives thereof for increasing the resistance of transgenic plant cells, intact plants and/or their progeny to pathogens.

Also encompassed in accordance with the invention is the use of at least one of the abovementioned enzymes, where an increased specific activity of at least one enzyme in comparison with the corresponding endogenous specific enzyme activity brings about an increase in the resistance of the plant cells or plants to pathogens by 20-90%, preferably by 30-80% and especially preferably by 40-70%.

In this context, the use of at least one of the enzymes according to the invention brings about, for example, an increased resistance to powdery mildews, preferably *Blumeria graminis* f. sp. *hordei* or f. sp. *tritici* and/or *Phytophtera infestans*.

The examples which follow are intended to illustrate the invention and are not limiting.

General Methods:

General DNA and cloning techniques, gel electrophoreses, sequencing, PCR, Northern blots, expression and purification of recombinant proteins, Western blots, HPLC and GC analyses and the cultivation of microorganisms are conventional laboratory methods and described, inter alia, in Sambrook et al. (Molecular cloning. A laboratory manual (1989) Cold Spring Harbor Laboratory Press).

The treatment of moss and plant material is likewise customary laboratory practice and described, inter alia, in Gelvin et al. (Plant Molecular Biology Manual, 1995, Dovdrecht/Holland, Kluwer Academic Publ.).

Cloning the Genes Encoding CYP74 Enzymes Via PCR

Two *Physcomitrella patens* lambda ZapII cDNA libraries, one from Protonematal and one from Gametophyte tissue, were available for the RACE-PCR. The T7-lang primer (5'-GTA ATA CGA CTC ACT ATA GGG CGA ATT GGG-3') acted as vector primer for the 5'-RACE-PCR. Standard methods were used.

For the nested RACE-PCR, a first PCR was carried out using M13rev primer (5'-GGA AAC AGC TAT GAC CAT G-3') and a RACE primer. This mixture acted as template for a second PCR with T7-lang primer and a (gene-specific) nested-RACE primer selected from amongst:

```
PP291AOS5R:   5'-TCA CCT CAT CCG ATA CGC TAG TC-3'
PP364AOS5R:   5'-GTC GAT GTC GTC TCA ATG TTC C-3'
PP364AOS5R2:  5'-CCA TTC GTG ATT GCC AGA ACT GC-3'
```

To clone the complete fragments, the latter were amplified with the aid of the Expand™ PCR system. In addition to the Taq polymerase, this system contains a Pwo polymerase with a proof-reading activity. The purpose of this second polymerase is to keep down the reading error rate in order to obtain as few mutations as possible in the DNA to be cloned. The following cDNA libraries were used as templates: Protonematal *P. patens* cDNA lambda ZapII and Gametophytic *P. patens* cDNA lambda ZapII. The following primers were employed:

```
PP291/5'SphI
5'-AAA GCA TGC ATG GCA GTC CCT TCA TCC AAG C-3'

PP291/3'PstI
5'-AAA CTG CAG TCA CTT TTT GAG ATC GGA AAA GAA AAC
CTT GGT CGC-3'

PP364/5'BamHI
5'-GGA TCC CGT ACG GTT GTA GCC AGT CTT GGG-3'

PP364/3'HindIII
5'-AAG CTT TCA ATC TGA TCG CGG CGT CAG TG-3'
```

To check the clones during the cloning of RACE and complete cDNAs, a process known as "colony" PCR with Tfl polymerase was carried out since the error rate was of no importance in this context. The primers were retained and the program was carried out using standard settings.

Isolation of the CYP74 Enzymes

Two genes encoding CYP74 enzymes were isolated from two *Physcomitrella patens* lambda ZapII cDNA libraries.

Clone Pp291

The clone Pp291 which was isolated had an open reading frame for 322 amino acids. This protein had 48% identity with a *Parthenium argentatum* AOS (Pan et al.; 1995, *J. Biol. Chem.* 270, 8487-8494). However, a comparison of its nucleotide sequence with other known AOSs revealed that approximately 500 to 650 bp were still missing at the 5' terminus. This is why a 5'-RACE-PCR was carried out with a lambda ZapII cDNA library from Protonematal tissue and with a lambda ZapII cDNA library from Gametophyte tissue. Using the RACE primer PP291AOS5R (see above) and an annealing temperature of 60° C., three fragments of different lengths were successfully amplified from the Protonematal library. An estimation of the fragment length was possible by comparison with the size standard also included in the agarose gel. The fragment lengths were 600 bp, 700 bp and 800 bp. The two longer fragments were cloned into the vector pGEM-T and sequenced. Both of the resulting sequences constituted an extension of the 5' terminus of the starting clone. A stop codon was located 15 bp upstream of the first start codon (ATG) in both of the sequences. To clone the complete cDNA, the expression primers (PP291/5'SphI and PP291/3'PstI, see above) with restriction cleavage sites for SphI and PstI were derived from the cDNA sequence of the RACE-PCR. The complete cDNA sequence obtained is shown in SEQ ID No. 1 and encodes a protein with 475 amino acids (SEQ ID No. 2).

Clone Pp364

The second cDNA clone contained an open reading frame which encoded a protein with 489 amino acids. This protein had 42% identity with the *Arabidopsis thaliana* AOS (Laudert et al.; 1996, *Plant Mol. Biol.* 31, 323-335) and 41% identity with the *L. usitatissimum* AOS, both at the amino acid level. Despite its length, this clone contained no start codon. The expression primers PP364/5'BamHI and PP364/3'HindIII with the restriction cleavage sites for BamHI and HindIII were derived from the known clone sequence. The complete cDNA sequence was obtained by RACE-PCR and inverted PCR. The complete cDNA sequence is shown in SEQ ID No. 3 and encodes a protein with 532 amino acids (SEQ ID No. 4).

Expression and Purification of Recombinant Proteins

In order to express the isolated cDNAs, they had to be ligated into an expression vector. The vector pQE30 (Qiagen, Hilden) was used in order to express proteins with N-terminal $His_6$-Tag. The ligation between pre-cut pQE30 and donor DNA (approximate ratio 3:1) was carried out with T4-DNA ligase.

The recombinant proteins were expressed in the *E. coli* strain SG13009 (Gottesmann et al.; 1981, *J. Bacteriol.* 148, 265-73). First, the expression clones were incubated at 37° C. in LB medium (with carbenicillin and kanamycin) until an $OD_{600}$ of 0.6-0.8 was reached. After induction with IPTG (final concentration 1 mM), the bacteria were grown for a further 2-3 days at 10° C.

As far as possible, the purification was carried out on ice, while the centrifugation steps were carried out at 4° C. The cells were sedimented by centrifugation for 15 minutes at 4000×g.

This cell sediment was resuspended completely in 50 mM sodium phosphate, pH 8, and sonicated (Sonopuls GM 70, Bandelin, Berlin) for 5×1 minute at 50% intensity and 50% pulse. The cell debris was removed by centrifugation in 15 minutes at 4000×g, and the cell membranes were sedimented from the supernatant by a further centrifugation (1 hour at 100 000×g).

In the case of both clones, Pp291 and Pp364, the recombinantly produced proteins were purified via affinity chromatography. This was followed by elution using a pH gradient (FIG. 1A) and, as an alternative, an imidazole gradient (FIG. 1B). Identical volumes (1 ml) were precipitated in all wash and elution steps and applied to the gel.

As can be seen from FIG. 1A, pure Pp291 protein was eluted from the column at a pH of 4. In the case of the imidazole gradient, the protein eluted in relatively pure form at an imidazole concentration of 100 mM and above. In comparison of the two methods, no difference was observed. This is why hereinbelow the protein was purified using the pH gradient only.

Activity Assays

Since sequence alignments do not allow conclusions regarding the catalytic activity, the products formed during the catalysis of the enzymes were analyzed by means of a photometric activity assay and by HPLC and GC analyses, all of which were carried out by standard methods.

In the photometric activity assay, the drop in absorption is measured at 234 nm. This drop is based on the breakdown of the conjugated diene system of the hydroperoxides during the reaction with Cyp74 enzymes. To this end, the respective substrate was dissolved (for the purposes of pure activity assay, generally to a final concentration of 20 µM 13-HPOTE or 9-HPODE) in phosphate buffer (the pH depending on the pH optimum of the enzyme) and the reaction was started by addition of the enzyme. The substrate concentration was monitored photometrically via the absorption at 234 nm. The molar absorption coefficient ($\lambda_{234\ nm}$) is 25 000 $M^{-1}$ $cm^{-1}$.

Figure 2:
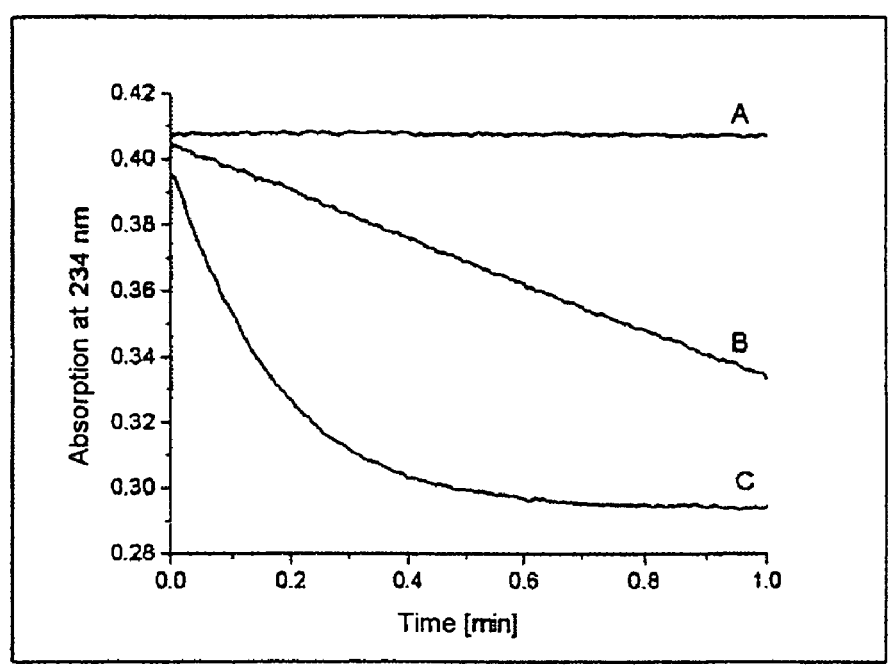
FIG. 2. Photometric activity assay.

Both substrates (13-HPOTE and 9-HPODE) were converted both by the enzyme encoded by clone Pp291 and by the enzyme encoded by clone Pp364. A graphic representation is shown in FIG. 2.

Figure 3:
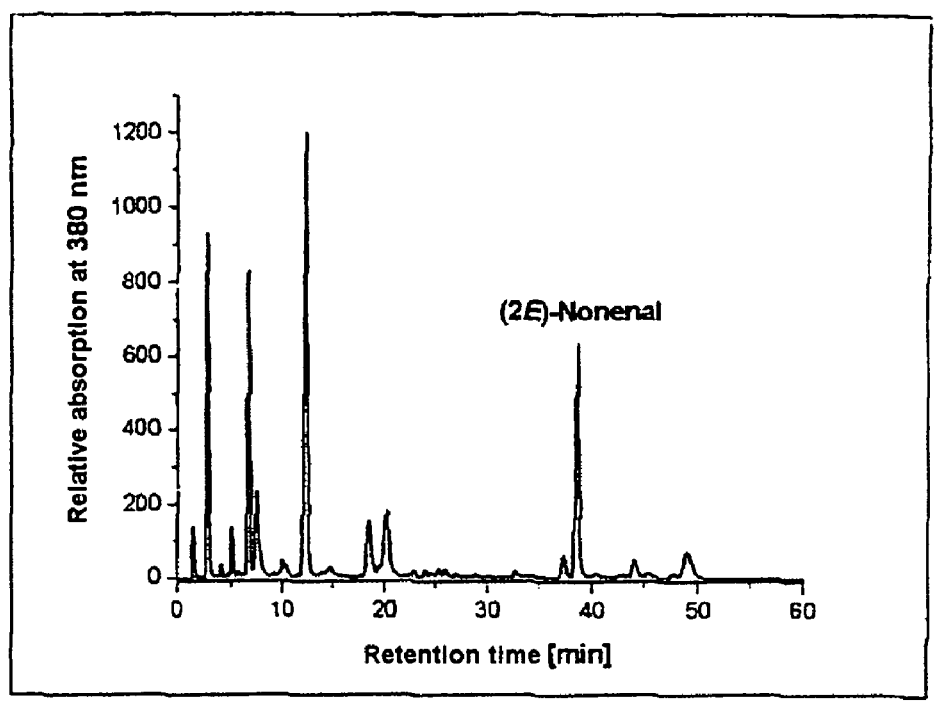
FIG. 3. Elution profile of HPLC analysis of hydrazones as derivatives of volatile aldehydes.

The reaction of hydroperoxides with DES gives rise to divinyl ethers which hydrolyze in an acidic environment to give aldehydes. These aldehydes are volatile. In order to identify these aldehydes which are formed, they can be derivatized with DNPH (Kohlmann et al.; 1999, *Eur. J. Biochem.* 260, 885-895). The hydrazones thus formed are no longer volatile and can be identified with the aid of an HPLC analysis via their retention time. As FIG. 3 shows, divinyl ethers, when treated with the derivatizing reagent, can also breakdown into aldehydes, which can then be detected in the form of DNPH derivatives.

Figure 4:
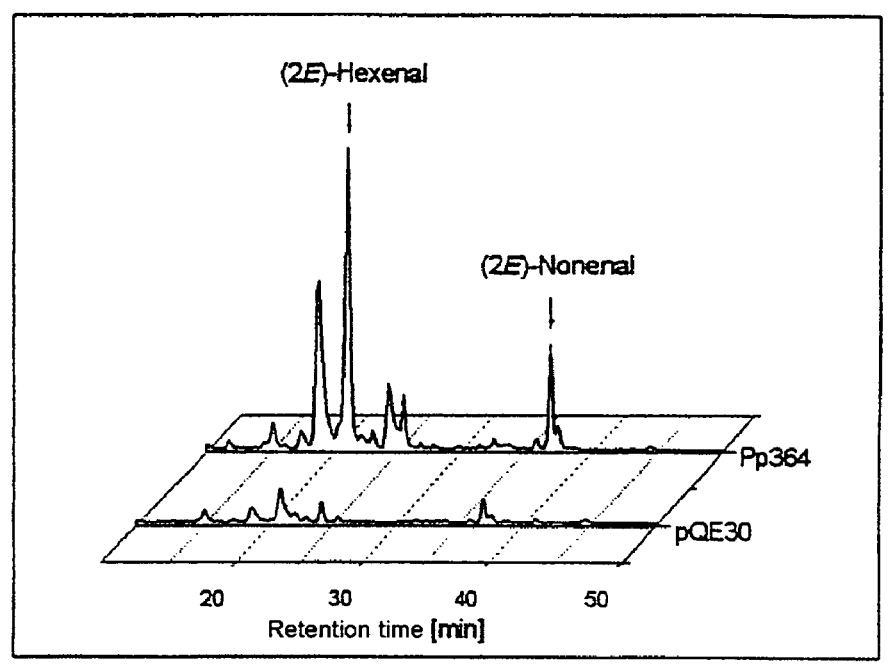
FIG. 4. Elution profile of HPLC analysis of catalysis products.

Using this method, it is possible to show that aldehydes are formed in the reaction mixture of the enzyme encoded by clone Pp364 and the substrates 13-HPOTE and 9-HPODE (FIG. 4). These aldehydes were identified by their retention times as (2E)-hexenal and (2E)-nonenal. They also revealed a UV spectrum which is typical of aldehyde-DNPH derivatives. No aldehydes were detected in the case of Pp291 (data not shown).

Figure 5:
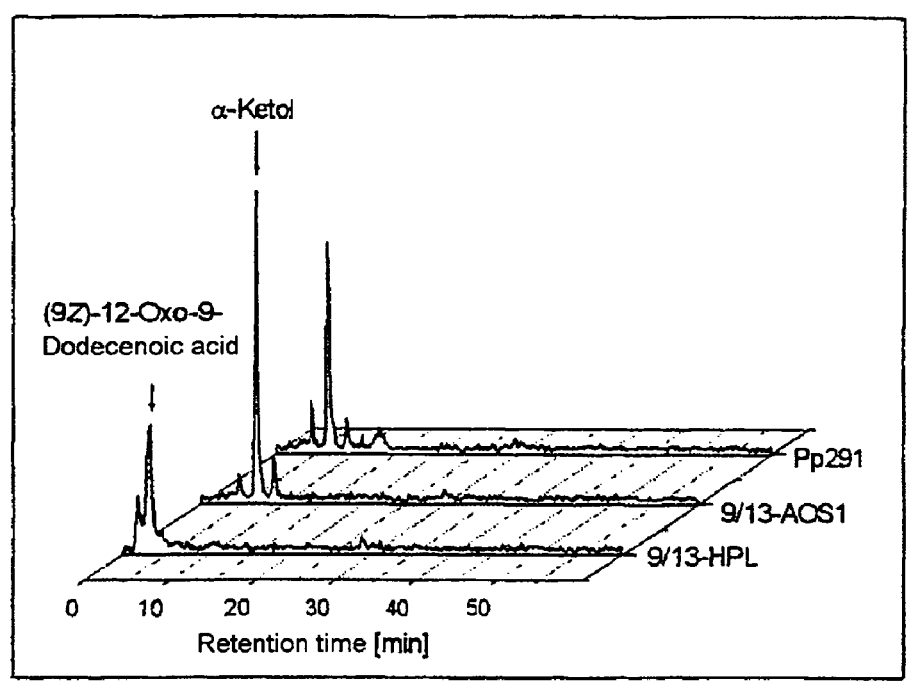
FIG. 5. Elution profile of HPLC analysis of nonvolatile products.

In the HPLC analysis of the non-volatile compounds, $1-^{14}C$-labeled hydroperoxides are reacted. Labeled products which can be visualized with the aid of a radio detector instead of a UV detector are formed. In this manner, even substances which have no typical UV maximum can be identified via their retention time. A further advantage is the fact that this type of detection is more sensitive than UV detection. If $[1-^{14}C$-13-HPOTE is employed as substrate in the enzyme reaction, the chromatogram shown in FIG. 5 reveals the same elution profile for Pp291 as for barley 9/13-AOS1 (Maucher et al.; 2000, *Plant J.* 21, 199-213), which was used as reference. It has already been demonstrated for other AOSs that the main reaction product in the absence of allene oxide cyclase is the α-ketol.

Figure 6:
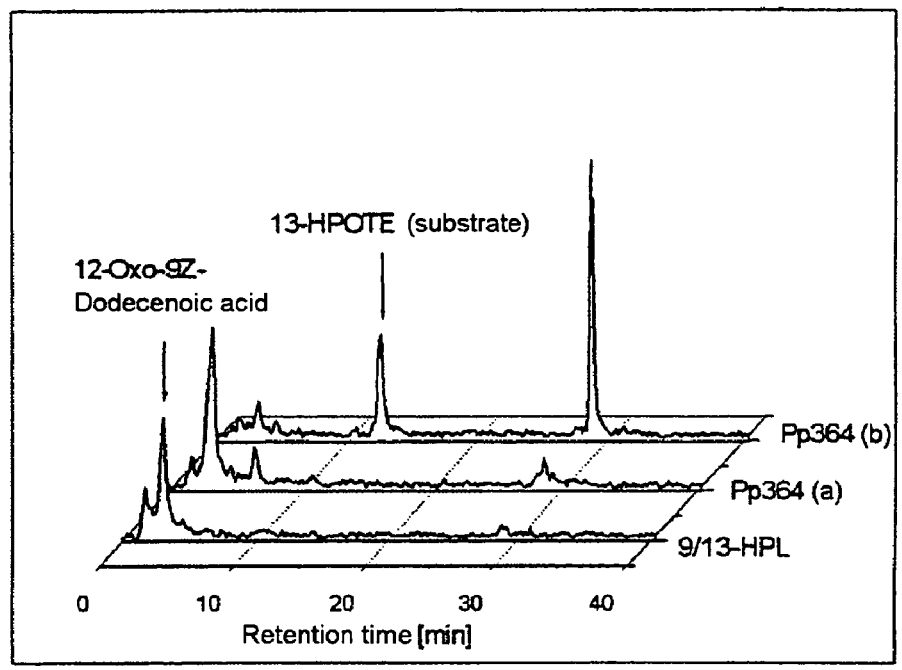
FIG. 6. Elution profile of HPLC analysis of nonvolatile products.

The chromatogram of the expression and the subsequent conversion of Pp364 showed a signal at approximately 30 minutes (FIG. 6). This signal was found neither in cucumber 9/13-HPL nor in barley 9/13-AOS1. Pp364 additionally showed other signals with the same retention time as the products of the cucumber 9/13-HPL.

Since, in radio-HPLC, liquid scintillator is added to the column eluate, the same HPLC run was carried out with unlabeled substrates in order to collect the products and to analyze them further. Since α-ketols have no typical UV maximum, the detection was carried out at 210 nm in this case (Gardner, 1997, *Advances in Lipid Methodology—four* (Christie, W. W., ed.) pp. 1-43, The Oily Press, Dundee).

Figure 7:
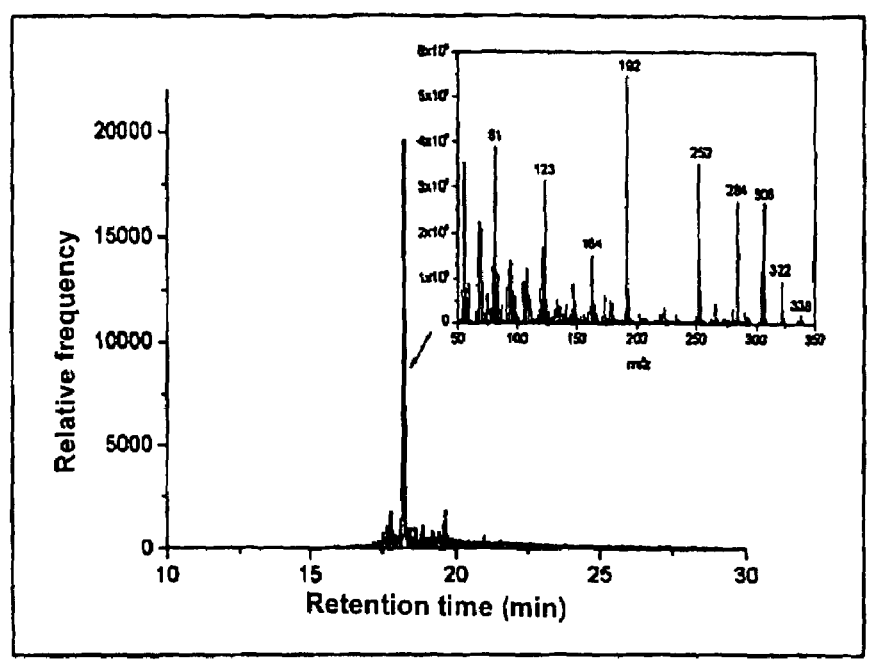
FIG. 7. BC/MS chromatogram of the product formed by catalysis of the CYP74 enzyme.

In the case of Pp291, a substance with the same retention time as the standard for the α-ketol formed from 13-HPOTE was collected, derivatized and studied with the aid of GC/MS. The chromatogram shown in (FIG. 7) resulted. The mass spectrum is identical with that of the corresponding α-ketol standard.

Determination of Enzyme Characteristics pH Optimum

Figure 8:
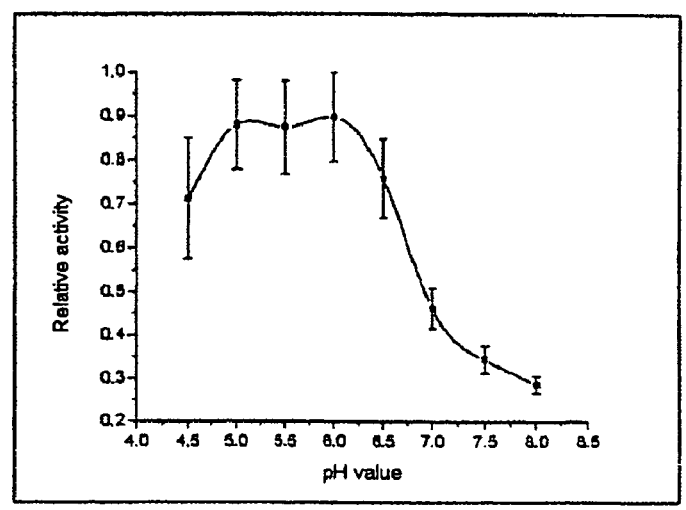
FIG. 8. Relative enzyme activity of the enzyme encoded by clone Pp291.

The pH optimum for clone Pp291 was determined photometrically. To this end, 13-HPOTE was used as substrate (approx. 25 µM in 50 mM sodium phosphate with the appropriate pH). The highest activity is shown by the enzyme in a pH range of between 5.0 and 6.0. This is shown in FIG. 8.

Enzyme-Kinetic Parameters

Figure 9:
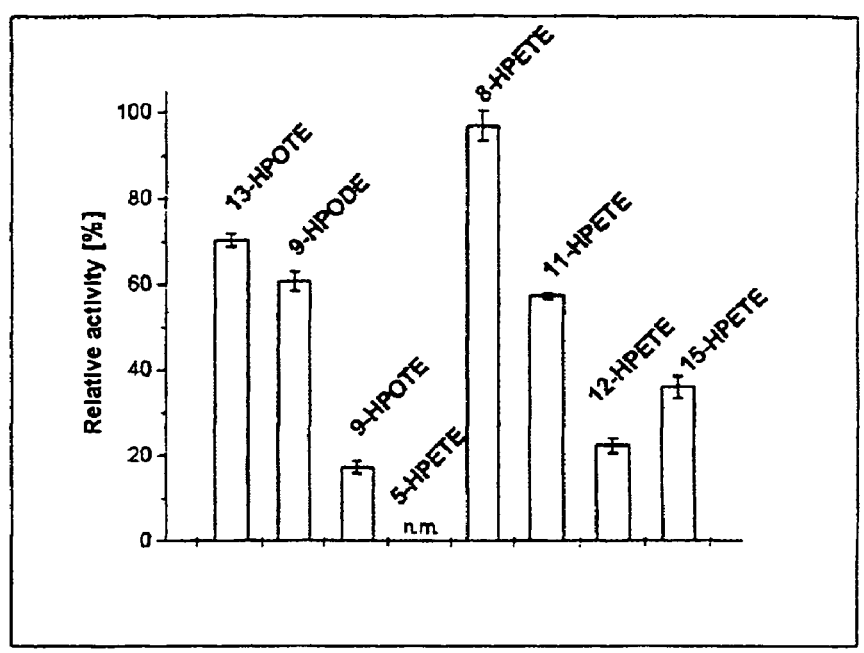
FIG. 9. Relative conversion rates of various substrates by the CYP74 enzyme.

Pp291 was studied with regard to its substrate specificity in particular regarding hydroperoxides of arachidonic acid (HPETE) since this is the predominant fatty acid of this organism (Girke et al.; 1998, *Plant J.* 15, 39-48). The ratio of the conversion rates shown in FIG. 9 were found. Among the hydroperoxides studied in the present context, 8-HPETE emerges as the substrate which is converted most rapidly. It is followed by 13-HPOTE, 9-HPODE and 11-HPETE in the ratio 8-HPETE:13-HPOTE:9-HPODE:11-HPETE, 100:70: 60:57.

Overexpression for Generating Increased Pathogen Resistance

For cloning the Pp291 and Pp364 cDNAs into binary vectors, they were restricted with BamHI and NotI and transferred into a BamHI- and NotI-cut pCRScript vector. They are subsequently excised from this vector using SalI and ligated into a suitably SalI-cut pBinAR vector. Those clones in which the genes are in sense orientation are determined by control excision with BamHI and sequencing.

Transformation into *Arabidopsis thaliana*:

Using these pBinAR vectors containing in each case a Pp291 and Pp364 cDNA in sense orientation, *Agrobacterium tumefaciens* (C58C1 pMP90) is transformed. Thereafter, wild-type *Arabidopsis thaliana* plants (cv. Columbia) are transformed with the respective transformed *Agrobacterium tumefaciens* strain on the basis of a modified method of the vacuum infiltration method of Clough and Bent (Clough S. and Bent A., Plant J 1998, 16(6):735-43) and Bechtold, et al. (Bechtold, N. et al., CRAcad Sci Paris 1993, 1144(2):204-212).

Seeds of the primary transformants are screened on the basis of the kanamycin resistance by planting seed on kanamycin-containing MS plates (MS medium (Sigma) supplemented with 40 mg/l kanamycin, 10 mg/l benomyl and 100 mg/l timentin). After 2 weeks, kanamycin-resistant seedlings are transferred into soil; when they have grown into fully developed plants they are used for phenotypic and molecular analysis.

Among the transgenic plants which have been transformed with Pp291 and Pp364 in sense orientation, those in which no cosuppression effect was observed were selected. To this end, total RNA is isolated from the plants, and the presence of the messenger is detected by means of real-time PCR (Perkin-Elmer). The transgenic plants identified thus were infected with various pathogens. These included *Blumeria grammis* f.sp. *hordei* and f.sp. *tritici*, *Pythium* spec., *Albugo* spec., *Rhizoctonia solani*, *Peronospora parasitica*, *Erysiphe crucifearum*, *E. cichoracearum*, *Alternaria brassicicola*, *Botrytis cinerea*, *Sclerotium rolfsii*, *Sclerotinia sclerotium*, *Fusarium oxysporum*, *F. culmorum*, *F. graminearum*, *F. nivale* or *Pseudomonas syringae*.

The result, i.e. the macroscopic degree of resistance of the plant to the pathogenic fungus or *bacterium*, was analyzed with the aid of fluorescence and light microscopy, inter alia. It emerged that the Pp291- and Pp364-transgenic *Arabidopsis* plants showed an increased resistance to the abovementioned pathogens in comparison with the wild type.

Transformation into Barley:

Barley cv. Pallas leaf segments were transformed with a cDNA of Pp291 or Pp364 which were present in the GFP expression vector (green fluorescence protein). The leaves were subsequently inoculated with the pathogenic fungus *Blumeria graminis* f.sp. *hordei* (powdery mildew of barley), and the result was analyzed after 48 hours by means of light microscopy and fluorescence microscopy. The penetration into GFP-expressing cells was assessed by detecting haustoria in live cells and by assessing the fungal development in precisely those cells. In all six experiments, bombardment of barley cv. Pallas with Pp291 or Pp364 cDNA resulted in a reduced number of cells which were successfully penetrated by *Blumeria graminis* f.sp. *hordei* (powdery mildew of barley) in comparison with cells which had been bombarded with a foreign control cDNA (human thyroid hormone receptor dsRNA, TR). The resistance-inducing effect of the Pp291 and Pp364 cDNA resulted in a reduced penetration efficiency by *Blumeria graminis* f.sp. *hordei* by 44% on average.

The transient transformation of barley was carried out with a method which had already been described for the biolistic introduction of cDNA into epidermal cells of barley leaves (Schweizer P et al. (1999) Mol Plant Microbe Interact 12:647-54; Schweizer P et al. (2000) Plant J 2000 24: 895-903). Tungsten particles with a diameter of 1.1 mm (particle density 25 mg/ml) were coated with cDNA together with plasmid DNA of the vector PGFP (GFP under the control of the CaMV 35S promoter) as transformation marker. To this end, the following amount of cDNA and reporter plasmid were used for coating purposes for each bombardment: 1 mg of pGFP and 2 mg of cDNA. To prepare the microcarriers, 55 mg of tungsten particles (M 17, diameter 1.1 mm; Bio-Rad, Munich) were washed twice with 1 ml of autoclave distilled water and once with 1 ml of absolute ethanol, dried and taken up in 1 ml of 50% strength glycerol (approximately 50 mg/ml stock solution). The solution was diluted with 50% strength glycerol to 25 mg/ml, mixed thoroughly before use and suspended in an ultrasonic bath. To coat the microcarriers, 1 mg of plasmid, 2 mg of cDNA (1 mL), 12.5 ml of tungsten particle suspension (25 mg/ml), 12.5 ml of 1 M Ca(NO3)2 solution (pH 10) per bombardment were combined dropwise with constant mixing, left to stand for 10 minutes at RT and centrifuged briefly, and 20 ml of supernatant were removed. The remainder, which contained the tungsten particles, is resuspended (ultrasonic bath) and employed in the experiment.

Barley primary leaf segments approximately 4 cm in length were used. The tissue was placed on 0.5% Phytagar (GibcoBRLt Life Technologiest, Karlsruhe) supplemented with 20 mg/ml benzimidazole in Petri dishes (diameter 6.5 cm); immediately prior to the particle bombardment, the edges were covered with a stencil with a rectangular slot 2.2 cm×2.3 cm in size. One after the other, the dishes were placed on the bottom of the vacuum chamber (Schweizer P et al. (1999) Mol Plant Microbe Interact 12:647-54) above which a nylon mesh (mesh size 0.2 mm, Millipore, Eschborn) had been inserted on a perforated board (5 cm above the bottom, 11 cm underneath the macrocarrier, see hereinbelow) to act as diffuser in order to diffuse particle aggregations and to slow down the particle stream. For each bombardment, the macrocarrier (plastic sterile filter holder 13 mm, Gelman Sciences, Swinney, UK) which had been attached at the top of the chamber was loaded with 5.8 ml of DNA-coated tungsten particles (microcarrier, see hereinbelow). The pressure in the chamber was reduced by 0.9 bar using a membrane vacuum pump (Vacuubrand, Wertheim), and the surface of the plant tissue was bombarded with the tungsten particles at a helium gas pressure of 9 bar. The chamber was aerated immediately thereafter.

To label transformed cells, the leaves were bombarded with the plasmid (pGFP; pUC18-based vector, CaMV 35S promoter/terminator cassette with inserted GFP gene; Schweizer P et al. (1999) Mol Plant Microbe Interact 12:647-54; provided by Dr P. Schweizer, Schweizer P, Institute of Plant Genetics IPK, Gatersleben, Germany). Before carrying out the bombardment with another plasmid, the macrocarrier was cleaned thoroughly with water in each case. After the leaves had been incubated for four hours post-bombardment at RT in daylight, with the Petri dishes being left slightly open, they were inoculated with 100 conidia/mm of the powdery mildew of barley fungus (race A6) and incubated for a further 40 to 48 hours under identical conditions.

Leaf segments were bombarded with the coated particles using a particle inflow gun. For each bombardment, 312 mg of tungsten particles were applied. 4 hours after the bombardment, the leaves were inoculated with *Blumeria graminis* mildew (race A6), and, after a further 40 hours, evaluated for infection symptoms. The result (for example the penetration efficiency, defined as percentage of attacked cells which form a mature haustorium and a secondary elongating hyphae; calculation: see hereinbelow) was analyzed by means of fluorescence microscopy and light microscopy. Inoculation with 100 conidia/mm2 results in an attack frequency of approximately 50% of the transformed cells. A minimum of 100 interaction sites was evaluated for each individual experiment. Transformed (GFP-expressing) cells were identified under excitation with blue light. Three different categories of transformed cells were distinguished:

1. penetrated cells containing a readily recognizable haustorium. A cell with more than one haustorium was rated as one cell.
2. Cells which, while attacked by a fungal appressorium, contain no haustorium. A cell which had been attacked repeatedly by *Blumeria graminis* ssp. hordeum, but which contains no haustorium, was rated as one cell.
3. Cells not attacked by *Blumeria graminis* ssp. hordeum.

Stomatol cells and subsidiary cells were not included in the evaluation. Surface structures of *Blumeria graminis* ssp. *hordeum* were analyzed by light microscopy and fluorescence staining of the fungus with 0.1% Calcofluor (w/v in water) for 30 seconds. The fungal development can be evaluated readily by fluorescence microscopy after staining with Calcofluor. While the fungus develops a primary and an appressorial germ tube in Pp291- or Pp364-dsRNA-transformed cells, no haustorial growth takes place. Haustorial development is a condition for the development of a secondary hypha.

The relative penetration efficiency (RPE) is calculated as the difference between the penetration efficiency in transformed cells (transformation with Pp291 or Pp364 cDNA) and the penetration efficiency in untransformed cells (here: average penetration efficiency 57%). The RPE in percent (% RPE) is calculated by subtracting 1 from the RPE and multiplying the result by 100.

RPE=[PE in transformed cells]

[PE in untransformed cells]

$$\% \ RPE = 100 \times (RPE - 1)$$

The % RPE value (deviation from the average penetration efficiency of the control) serves to determine the susceptibility of cells transformed with pp291 or Pp364 cDNA.

In five independent experiments, the control cDNA revealed no difference between the transfection with the control cDNA and water with regard to the penetration efficiency of *Blumeria graminis* ssp. *hordeum.*

To rule out an effect of the cDNA on the transformation rate or survival rate of the attacked cells, the number of GFP-expressing cells between control and Pp291, or Pp364, cDNA experiments was compared. The Pp291 and Pp364 cDNA had no effect on the total number or the number of attacked GFP-expressing cells.

The transfection rate with Pp291 and Pp364 resulted in a drastic drop in the penetration frequency of *Blumeria graminis* f.sp. *hordei* (average % RPE value=−30%).

We claim:

1. An isolated allene oxide synthase with the amino acid sequence of SEQ ID NO: 2.

2. An isolated divinyl ether synthase with the amino acid sequence of SEQ ID NO: 4.

3. The isolated allene oxide synthase of claim 1 which converts both 9-HPOD/TE and 13-HPOD/TE as substrates.

4. A method for increasing resistance of a plant cell, plant or progeny thereof to a pathogen, the method comprising administering the isolated allene oxide synthase of claim 1 to said plant cell, plant or progeny thereof.

5. The method of claim 4, wherein the administering of the synthase results in an increase in resistance to the pathogen by 20-90% when compared to the pathogen resistance shown in a corresponding untreated plant cell, plant, or progeny thereof.

6. The method of claim 4, wherein the administering of the synthase results in an increased resistance to mildew.

7. The isolated divinyl ether synthase of claim 2, which converts both 9-HPOD/TE and 13-HPOD/TE as substrates.

8. A method for increasing resistance of a plant cell, plant or progeny thereof to a pathogen, the method comprising administering the isolated divinyl ether synthase of claim 2 to said plant cell, plant or progeny thereof.

9. The method of claim 8, wherein the administering of the synthase results in an increase in resistance to the pathogen by 20-90% when compared to the pathogen resistance shown in a corresponding untreated plant cell, plant, or progeny thereof.

10. The method of claim 5, wherein the increase in resistance to the pathogen is 30-80%.

11. The method of claim 9, wherein the increase in resistance to the pathogen is 30-80%.

12. The method of claim 5, wherein the increase in resistance to the pathogen is 40-70%.

13. The method of claim 9, wherein the increase in resistance to the pathogen is 40-70%.

14. The method of claim 8, wherein the administering of the synthase results in an increased resistance to mildew.

15. The method of claim 6, wherein the mildew is caused by *Blumeria graminis*, *Blumeria hordei*, *Blumeria tritici* or *Phytophtora infestans*.

16. The method of claim 14, wherein the mildew is caused by *Blumeria graminis*, *Blumeria hordei*, *Blumeria tritici* or *Phytophtora infestans*.

* * * * *

SEQUENCE LISTING

```
<160> NUMBER OF SEQ ID NOS: 13

<210> SEQ ID NO 1
<211> LENGTH: 1428
<212> TYPE: DNA
<213> ORGANISM: Physcomitrella patens
<220> FEATURE:
<221> NAME/KEY: CDS
<222> LOCATION: (1)..(1428)
<223> OTHER INFORMATION: Pp291 Allenoxid-Synthase

<400> SEQUENCE: 1 atg gca gtc cct tca tcc aag ctg ccg ttg aag gcg att cct gga gac        48
Met Ala Val Pro Ser Ser Lys Leu Pro Leu Lys Ala Ile Pro Gly Asp
1               5                   10                  15 tat gga gtc ccc tac ttc ggt gcc ata aag gat cga cta gac tac ttt        96
Tyr Gly Val Pro Tyr Phe Gly Ala Ile Lys Asp Arg Leu Asp Tyr Phe
            20                  25                  30 tgg ttg cag ggg gag gag cag ttt tac cga agc cgg atg gcc aag tac       144
Trp Leu Gln Gly Glu Glu Gln Phe Tyr Arg Ser Arg Met Ala Lys Tyr
        35                  40                  45 aat agc acg gtg ttt cgt gtc aac atg ccg cct ggc cct cca att tcc       192
Asn Ser Thr Val Phe Arg Val Asn Met Pro Pro Gly Pro Pro Ile Ser
    50                  55                  60 gaa cac cct caa gtc atc tgc ctc ttg gat cag aaa agc ttt cca att       240
Glu His Pro Gln Val Ile Cys Leu Leu Asp Gln Lys Ser Phe Pro Ile
65                  70                  75                  80 ctg ttc gac gtt agc aag gtt gag aaa aag gac gtg ttc aca gga aca       288
Leu Phe Asp Val Ser Lys Val Glu Lys Lys Asp Val Phe Thr Gly Thr
```

-continued

```
                    85                  90                  95
tac atg ccg agt gtg agc ttc acc agc ggg tac cgc gtt tgc tcc tac      336
Tyr Met Pro Ser Val Ser Phe Thr Ser Gly Tyr Arg Val Cys Ser Tyr
            100                 105                 110 ttg gat ccc tct gag gaa cgc cac acg aag ctc aag caa tgg tgc ttt      384
Leu Asp Pro Ser Glu Glu Arg His Thr Lys Leu Lys Gln Trp Cys Phe
        115                 120                 125 gaa gtc att gcg atg aac ggg cgg aac ttt ctt ccc gag ttt cac aag      432
Glu Val Ile Ala Met Asn Gly Arg Asn Phe Leu Pro Glu Phe His Lys
    130                 135                 140 tcg att gaa gag tcg atg gtg ctc tgg gag acg agt ctg gcc aag ggc      480
Ser Ile Glu Glu Ser Met Val Leu Trp Glu Thr Ser Leu Ala Lys Gly
145                 150                 155                 160 gag aag act agc gta tcg gat gag gtg aaa cag ttc gcg ttt aat ttc      528
Glu Lys Thr Ser Val Ser Asp Glu Val Lys Gln Phe Ala Phe Asn Phe
                165                 170                 175 ctg atg cgc gct gta tgc cat cac gac ccc gct gcg cct gga gaa tac      576
Leu Met Arg Ala Val Cys His His Asp Pro Ala Ala Pro Gly Glu Tyr
            180                 185                 190 agc tta ggg cgt aat ggt ggc ccg tat gca acc gcc tgg gca aat ccc      624
Ser Leu Gly Arg Asn Gly Gly Pro Tyr Ala Thr Ala Trp Ala Asn Pro
        195                 200                 205 cag ctc gct ccg att gca gga cag acg ggt ctc ccc cat gtc gtg gag      672
Gln Leu Ala Pro Ile Ala Gly Gln Thr Gly Leu Pro His Val Val Glu
    210                 215                 220 gag ctc gtg tta cac acc gtc cca ctc ccc tct gcc ctg gtc aag aag      720
Glu Leu Val Leu His Thr Val Pro Leu Pro Ser Ala Leu Val Lys Lys
225                 230                 235                 240 aac tac gat gcc ctc tac aat ttc atc aaa aac tac gcc acc gag gcg      768
Asn Tyr Asp Ala Leu Tyr Asn Phe Ile Lys Asn Tyr Ala Thr Glu Ala
                245                 250                 255 ctg gat agg gct gaa gct atg ggc atc gag cgc aat gac gcc act gcc      816
Leu Asp Arg Ala Glu Ala Met Gly Ile Glu Arg Asn Asp Ala Thr Ala
            260                 265                 270 aac ctg ctg ttc ttc ctt tgc ttt aac gcc tac ggc gga ttc agc atc      864
Asn Leu Leu Phe Phe Leu Cys Phe Asn Ala Tyr Gly Gly Phe Ser Ile
        275                 280                 285 ttc ttc ccc ctc atc act atc ctc att tct tca tgc ggt ccg gag ctc      912
Phe Phe Pro Leu Ile Thr Ile Leu Ile Ser Ser Cys Gly Pro Glu Leu
    290                 295                 300 atg cac gat ctc cac gac gaa gtc acc aag gcc gtc gcc gcc aca gat      960
Met His Asp Leu His Asp Glu Val Thr Lys Ala Val Ala Ala Thr Asp
305                 310                 315                 320 ggg aaa gtc act ctt caa tcc atc gag aac atg cca ttg gtg aag tcc     1008
Gly Lys Val Thr Leu Gln Ser Ile Glu Asn Met Pro Leu Val Lys Ser
                325                 330                 335 gtc gtc tac gaa gct ttc cga ttc aag ccc cca gtg cca tac caa tac     1056
Val Val Tyr Glu Ala Phe Arg Phe Lys Pro Pro Val Pro Tyr Gln Tyr
            340                 345                 350 ggc aag gcc aag ttc gac ttc acc ata gag aac cac gaa aac tcc ttc     1104
Gly Lys Ala Lys Phe Asp Phe Thr Ile Glu Asn His Glu Asn Ser Phe
        355                 360                 365 gag gtc aag aag gga gaa atg ctg tat ggt tat caa cct atc gtg atg     1152
Glu Val Lys Lys Gly Glu Met Leu Tyr Gly Tyr Gln Pro Ile Val Met
    370                 375                 380 cac gac ccc aag gtc ttc tcg gac cca gat cag ttt cta cct cga cga     1200
His Asp Pro Lys Val Phe Ser Asp Pro Asp Gln Phe Leu Pro Arg Arg
385                 390                 395                 400 ttc atg ggc ccc gac ggc gag aag ctc atc aaa tac atc ttc tgg tcc     1248
Phe Met Gly Pro Asp Gly Glu Lys Leu Ile Lys Tyr Ile Phe Trp Ser
```

```
Phe Met Gly Pro Asp Gly Glu Lys Leu Ile Lys Tyr Ile Phe Trp Ser
            405                 410                 415 aat ggt tac gag act gac gag ccg act acc gca aac aag cag tgc gcc      1296
Asn Gly Tyr Glu Thr Asp Glu Pro Thr Thr Ala Asn Lys Gln Cys Ala
            420                 425                 430 gga aag gac ttg gtg gtc aca atg gcg cga gca ttc gtc gca gaa atg      1344
Gly Lys Asp Leu Val Val Thr Met Ala Arg Ala Phe Val Ala Glu Met
            435                 440                 445 ttc ttg aga tat aaa gag tat acc ctg acc atg gag ggc gca gga aat      1392
Phe Leu Arg Tyr Lys Glu Tyr Thr Leu Thr Met Glu Gly Ala Gly Asn
        450                 455                 460 gcg acc aag gtt ttc ttt tcc gat ctc aaa aag tga                      1428
Ala Thr Lys Val Phe Phe Ser Asp Leu Lys Lys
465                 470                 475

<210> SEQ ID NO 2
<211> LENGTH: 475
<212> TYPE: PRT
<213> ORGANISM: Physcomitrella patens

<400> SEQUENCE: 2

Met Ala Val Pro Ser Ser Lys Leu Pro Leu Lys Ala Ile Pro Gly Asp
1               5                   10                  15

Tyr Gly Val Pro Tyr Phe Gly Ala Ile Lys Asp Arg Leu Asp Tyr Phe
            20                  25                  30

Trp Leu Gln Gly Glu Glu Gln Phe Tyr Arg Ser Arg Met Ala Lys Tyr
        35                  40                  45

Asn Ser Thr Val Phe Arg Val Asn Met Pro Pro Gly Pro Pro Ile Ser
    50                  55                  60

Glu His Pro Gln Val Ile Cys Leu Leu Asp Gln Lys Ser Phe Pro Ile
65                  70                  75                  80

Leu Phe Asp Val Ser Lys Val Glu Lys Lys Asp Val Phe Thr Gly Thr
                85                  90                  95

Tyr Met Pro Ser Val Ser Phe Thr Ser Gly Tyr Arg Val Cys Ser Tyr
            100                 105                 110

Leu Asp Pro Ser Glu Glu Arg His Thr Lys Leu Lys Gln Trp Cys Phe
        115                 120                 125

Glu Val Ile Ala Met Asn Gly Arg Asn Phe Leu Pro Glu Phe His Lys
    130                 135                 140

Ser Ile Glu Glu Ser Met Val Leu Trp Glu Thr Ser Leu Ala Lys Gly
145                 150                 155                 160

Glu Lys Thr Ser Val Ser Asp Glu Val Lys Gln Phe Ala Phe Asn Phe
                165                 170                 175

Leu Met Arg Ala Val Cys His His Asp Pro Ala Ala Pro Gly Glu Tyr
            180                 185                 190

Ser Leu Gly Arg Asn Gly Gly Pro Tyr Ala Thr Ala Trp Ala Asn Pro
        195                 200                 205

Gln Leu Ala Pro Ile Ala Gly Gln Thr Gly Leu Pro His Val Val Glu
    210                 215                 220

Glu Leu Val Leu His Thr Val Pro Leu Pro Ser Ala Leu Val Lys Lys
225                 230                 235                 240

Asn Tyr Asp Ala Leu Tyr Asn Phe Ile Lys Asn Tyr Ala Thr Glu Ala
                245                 250                 255

Leu Asp Arg Ala Glu Ala Met Gly Ile Glu Arg Asn Asp Ala Thr Ala
            260                 265                 270

Asn Leu Leu Phe Phe Leu Cys Phe Asn Ala Tyr Gly Gly Phe Ser Ile
```

-continued

```
                       275                 280                 285
Phe Phe Pro Leu Ile Thr Ile Leu Ile Ser Ser Cys Gly Pro Glu Leu
    290                 295                 300

Met His Asp Leu His Asp Glu Val Thr Lys Ala Val Ala Ala Thr Asp
305                 310                 315                 320

Gly Lys Val Thr Leu Gln Ser Ile Glu Asn Met Pro Leu Val Lys Ser
                325                 330                 335

Val Val Tyr Glu Ala Phe Arg Phe Lys Pro Val Pro Tyr Gln Tyr
                340                 345                 350

Gly Lys Ala Lys Phe Asp Phe Thr Ile Glu Asn His Glu Asn Ser Phe
                355                 360                 365

Glu Val Lys Lys Gly Glu Met Leu Tyr Gly Tyr Gln Pro Ile Val Met
    370                 375                 380

His Asp Pro Lys Val Phe Ser Asp Pro Asp Gln Phe Leu Pro Arg Arg
385                 390                 395                 400

Phe Met Gly Pro Asp Gly Glu Lys Leu Ile Lys Tyr Ile Phe Trp Ser
                405                 410                 415

Asn Gly Tyr Glu Thr Asp Glu Pro Thr Thr Ala Asn Lys Gln Cys Ala
                420                 425                 430

Gly Lys Asp Leu Val Val Thr Met Ala Arg Ala Phe Val Ala Glu Met
                435                 440                 445

Phe Leu Arg Tyr Lys Glu Tyr Thr Leu Thr Met Glu Gly Ala Gly Asn
    450                 455                 460

Ala Thr Lys Val Phe Phe Ser Asp Leu Lys Lys
465                 470                 475

<210> SEQ ID NO 3
<211> LENGTH: 1821
<212> TYPE: DNA
<213> ORGANISM: Physcomitrella patens
<220> FEATURE:
<221> NAME/KEY: CDS
<222> LOCATION: (25)..(1623)
<223> OTHER INFORMATION: Pp364 Divinylether-Synthase

<400> SEQUENCE: 3
gcggaaaact ccgctccgat caat atg gat cgc act tta gtt ctg act tgc       51
                         Met Asp Arg Thr Leu Val Leu Thr Cys
                          1               5 act acg act tgc agc cac tcc gca ttc cgc cag tct gca ttg cct agc      99
Thr Thr Thr Cys Ser His Ser Ala Phe Arg Gln Ser Ala Leu Pro Ser
 10                  15                  20                  25 aac acc agc ata tct gtg agg tta gga aca tgt agc gtt cgc aca cag    147
Asn Thr Ser Ile Ser Val Arg Leu Gly Thr Cys Ser Val Arg Thr Gln
                 30                  35                  40 aag cgc cgt acg gtt gta gcc agt ctt ggg aac att gag acg aca tcg    195
Lys Arg Arg Thr Val Val Ala Ser Leu Gly Asn Ile Glu Thr Thr Ser
             45                  50                  55 aca tcg acc gtg ggg caa gag agc aat ctg ccc ctc cgt gaa atc ccc    243
Thr Ser Thr Val Gly Gln Glu Ser Asn Leu Pro Leu Arg Glu Ile Pro
         60                  65                  70 gga agc tac gga atc cct tat ttg tcg caa ttg ctc gac aga tgg acc    291
Gly Ser Tyr Gly Ile Pro Tyr Leu Ser Gln Leu Leu Asp Arg Trp Thr
     75                  80                  85 ttt ttt tac agg gaa ggc gaa ccg cag ttc tgg caa tca cga atg gcg    339
Phe Phe Tyr Arg Glu Gly Glu Pro Gln Phe Trp Gln Ser Arg Met Ala
 90                  95                 100                 105 aag tat ggg agc acc gtg att cga tcc aac atg ccg cct ggt tgg ttt    387
```

-continued

```
                Lys Tyr Gly Ser Thr Val Ile Arg Ser Asn Met Pro Pro Gly Trp Phe
                                110                 115                 120 tgg acc gac tcc cgc tgc att atg ctt ctt gac cag aag agc tac ccc              435
Trp Thr Asp Ser Arg Cys Ile Met Leu Leu Asp Gln Lys Ser Tyr Pro
            125                 130                 135 acc gtc ttt gat tac gat aag gtg gat aag tac aaa gcc ttt gct ggg              483
Thr Val Phe Asp Tyr Asp Lys Val Asp Lys Tyr Lys Ala Phe Ala Gly
            140                 145                 150 acc atc atg cca agc acc gaa tac aat ggc ggg tat gag gtg tgt gcg              531
Thr Ile Met Pro Ser Thr Glu Tyr Asn Gly Gly Tyr Glu Val Cys Ala
            155                 160                 165 tac ctc gac gct tct gac aag aag cat gag cag ctc aaa ggc tat tgc              579
Tyr Leu Asp Ala Ser Asp Lys Lys His Glu Gln Leu Lys Gly Tyr Cys
170                 175                 180                 185 ttc gag ctt ctc aaa ttt tcc tcg tcg aaa tgg gca cgg gag ttt cac              627
Phe Glu Leu Leu Lys Phe Ser Ser Ser Lys Trp Ala Arg Glu Phe His
                190                 195                 200 acg gcc atc tca gag aca ttc aat cag tgg gaa ggc aaa ctt gca caa              675
Thr Ala Ile Ser Glu Thr Phe Asn Gln Trp Glu Gly Lys Leu Ala Gln
                205                 210                 215 aag acg cct gca tta att aac ccg acg ctt cct gaa tcg ctc ttt agt              723
Lys Thr Pro Ala Leu Ile Asn Pro Thr Leu Pro Glu Ser Leu Phe Ser
            220                 225                 230 ttt gtg atc aat gca ctg act acc gct aga ttc gac gac agt agc ata              771
Phe Val Ile Asn Ala Leu Thr Thr Ala Arg Phe Asp Asp Ser Ser Ile
235                 240                 245 ccc gat gca gag aag cca gtc tgc ggg gat ttg caa aaa tgg gcg gga              819
Pro Asp Ala Glu Lys Pro Val Cys Gly Asp Leu Gln Lys Trp Ala Gly
250                 255                 260                 265 ttc cag ctg atg ccc gta atc aga acc ggg gca cct atc tac att gaa              867
Phe Gln Leu Met Pro Val Ile Arg Thr Gly Ala Pro Ile Tyr Ile Glu
                270                 275                 280 gag atg ctc cac gtt gct ccc atc cct gca agc cta act aaa ggg ggc              915
Glu Met Leu His Val Ala Pro Ile Pro Ala Ser Leu Thr Lys Gly Gly
                285                 290                 295 tat gac aaa atg gtg gtg ttt ctt caa aag tat gcg gct gaa acg cta              963
Tyr Asp Lys Met Val Val Phe Leu Gln Lys Tyr Ala Ala Glu Thr Leu
            300                 305                 310 tcc atc gca gag aag ttt ggg ttg tct cag gac gag gcg gtt cac aac             1011
Ser Ile Ala Glu Lys Phe Gly Leu Ser Gln Asp Glu Ala Val His Asn
            315                 320                 325 ttg atc ttc ttc cta atc ttg aac gct cat ggc gga ttc tgc cgg ttc             1059
Leu Ile Phe Phe Leu Ile Leu Asn Ala His Gly Gly Phe Cys Arg Phe
330                 335                 340                 345 ctt cca gtg atc ctt cgg gaa gta gcc aag aat ggc caa ctg caa gct             1107
Leu Pro Val Ile Leu Arg Glu Val Ala Lys Asn Gly Gln Leu Gln Ala
                350                 355                 360 gat ttg cga gag gaa gtg cgg gcc gca gtg aaa gcc agc gga tcg gac             1155
Asp Leu Arg Glu Glu Val Arg Ala Ala Val Lys Ala Ser Gly Ser Asp
                365                 370                 375 caa gtg acc atg aag gcc gtg atg aat gac atg cct ctg gtg gca tcg             1203
Gln Val Thr Met Lys Ala Val Met Asn Asp Met Pro Leu Val Ala Ser
            380                 385                 390 aca gta ttc gag gcg ctc cgc ttc gac ccc ccg gtg cca ttt cag tac             1251
Thr Val Phe Glu Ala Leu Arg Phe Asp Pro Pro Val Pro Phe Gln Tyr
395                 400                 405 gcc aga gcg aag aag gac ttc atc atc gaa tcc cac gac gcg aga tac             1299
Ala Arg Ala Lys Lys Asp Phe Ile Ile Glu Ser His Asp Ala Arg Tyr
410                 415                 420                 425
```

```
caa ata aaa acc ggc gac ttc ctc ggc ggc gtg aac tac atg gtc tcc    1347
Gln Ile Lys Thr Gly Asp Phe Leu Gly Gly Val Asn Tyr Met Val Ser
                430                 435                 440 cgc gac ccg aag gtg ttc acc gac agg ccc aac gag ttc aac gcg cgg    1395
Arg Asp Pro Lys Val Phe Thr Asp Arg Pro Asn Glu Phe Asn Ala Arg
        445                 450                 455 cgg ttc atg gga ccg gag ggg gac aag ctg ctt gca cat ttg gtg tgg    1443
Arg Phe Met Gly Pro Glu Gly Asp Lys Leu Leu Ala His Leu Val Trp
    460                 465                 470 tcg aac ggc cgg caa act gat gaa acc acg gtg tac aca aag cag tgt    1491
Ser Asn Gly Arg Gln Thr Asp Glu Thr Thr Val Tyr Thr Lys Gln Cys
475                 480                 485 gcg ggg aag gag att gtg ccg ctc aca ggg cgc ctt ctt ctg gcg gag    1539
Ala Gly Lys Glu Ile Val Pro Leu Thr Gly Arg Leu Leu Leu Ala Glu
490                 495                 500                 505 ctt ttc atg cgc ttc gat tcc ttc aac atc gaa ggc ctc gaa atg gag    1587
Leu Phe Met Arg Phe Asp Ser Phe Asn Ile Glu Gly Leu Glu Met Glu
                510                 515                 520 gca acc ttc act tca ctg acg ccg cga tca gat tga agctatagct         1633
Ala Thr Phe Thr Ser Leu Thr Pro Arg Ser Asp
                525                 530 tgtaaaacac ccaccccacg ttgtgagatt attagtacca cgtacatcag tagttcacga  1693
gactcatatt ctgatccatc atcgcctgga tgtcgaaact gactatatgt agtatactcg  1753
actttgtatg ccaaaaacac attttcaatt tgtctaatcg gccctgtttc cacttcaaaa  1813
aaaaaaaa                                                           1821

<210> SEQ ID NO 4
<211> LENGTH: 532
<212> TYPE: PRT
<213> ORGANISM: Physcomitrella patens

<400> SEQUENCE: 4

Met Asp Arg Thr Leu Val Leu Thr Cys Thr Thr Cys Ser His Ser
1               5                   10                  15

Ala Phe Arg Gln Ser Ala Leu Pro Ser Asn Thr Ser Ile Ser Val Arg
            20                  25                  30

Leu Gly Thr Cys Ser Val Arg Thr Gln Lys Arg Arg Thr Val Val Ala
        35                  40                  45

Ser Leu Gly Asn Ile Glu Thr Thr Ser Thr Ser Thr Val Gly Gln Glu
    50                  55                  60

Ser Asn Leu Pro Leu Arg Glu Ile Pro Gly Ser Tyr Gly Ile Pro Tyr
65                  70                  75                  80

Leu Ser Gln Leu Leu Asp Arg Trp Thr Phe Phe Tyr Arg Glu Gly Glu
                85                  90                  95

Pro Gln Phe Trp Gln Ser Arg Met Ala Lys Tyr Gly Ser Thr Val Ile
            100                 105                 110

Arg Ser Asn Met Pro Pro Gly Trp Phe Trp Thr Asp Ser Arg Cys Ile
        115                 120                 125

Met Leu Leu Asp Gln Lys Ser Tyr Pro Thr Val Phe Asp Tyr Asp Lys
    130                 135                 140

Val Asp Lys Tyr Lys Ala Phe Ala Gly Thr Ile Met Pro Ser Thr Glu
145                 150                 155                 160

Tyr Asn Gly Gly Tyr Glu Val Cys Ala Tyr Leu Asp Ala Ser Asp Lys
                165                 170                 175

Lys His Glu Gln Leu Lys Gly Tyr Cys Phe Glu Leu Leu Lys Phe Ser
            180                 185                 190
```

```
Ser Ser Lys Trp Ala Arg Glu Phe His Thr Ala Ile Ser Glu Thr Phe
    195                 200                 205
Asn Gln Trp Glu Gly Lys Leu Ala Gln Lys Thr Pro Ala Leu Ile Asn
    210                 215                 220
Pro Thr Leu Pro Glu Ser Leu Phe Ser Phe Val Ile Asn Ala Leu Thr
225                 230                 235                 240
Thr Ala Arg Phe Asp Asp Ser Ser Ile Pro Asp Ala Glu Lys Pro Val
                245                 250                 255
Cys Gly Asp Leu Gln Lys Trp Ala Gly Phe Gln Leu Met Pro Val Ile
                260                 265                 270
Arg Thr Gly Ala Pro Ile Tyr Ile Glu Glu Met Leu His Val Ala Pro
                275                 280                 285
Ile Pro Ala Ser Leu Thr Lys Gly Gly Tyr Asp Lys Met Val Val Phe
                290                 295                 300
Leu Gln Lys Tyr Ala Ala Glu Thr Leu Ser Ile Ala Glu Lys Phe Gly
305                 310                 315                 320
Leu Ser Gln Asp Glu Ala Val His Asn Leu Ile Phe Phe Leu Ile Leu
                325                 330                 335
Asn Ala His Gly Gly Phe Cys Arg Phe Leu Pro Val Ile Leu Arg Glu
                340                 345                 350
Val Ala Lys Asn Gly Gln Leu Gln Ala Asp Leu Arg Glu Glu Val Arg
                355                 360                 365
Ala Ala Val Lys Ala Ser Gly Ser Asp Gln Val Thr Met Lys Ala Val
                370                 375                 380
Met Asn Asp Met Pro Leu Val Ala Ser Thr Val Phe Glu Ala Leu Arg
385                 390                 395                 400
Phe Asp Pro Pro Val Pro Phe Gln Tyr Ala Arg Ala Lys Lys Asp Phe
                405                 410                 415
Ile Ile Glu Ser His Asp Ala Arg Tyr Gln Ile Lys Thr Gly Asp Phe
                420                 425                 430
Leu Gly Gly Val Asn Tyr Met Val Ser Arg Asp Pro Lys Val Phe Thr
                435                 440                 445
Asp Arg Pro Asn Glu Phe Asn Ala Arg Arg Phe Met Gly Pro Glu Gly
                450                 455                 460
Asp Lys Leu Leu Ala His Leu Val Trp Ser Asn Gly Arg Gln Thr Asp
465                 470                 475                 480
Glu Thr Thr Val Tyr Thr Lys Gln Cys Ala Gly Lys Glu Ile Val Pro
                485                 490                 495
Leu Thr Gly Arg Leu Leu Ala Glu Leu Phe Met Arg Phe Asp Ser
                500                 505                 510
Phe Asn Ile Glu Gly Leu Glu Met Glu Ala Thr Phe Thr Ser Leu Thr
                515                 520                 525
Pro Arg Ser Asp
    530

<210> SEQ ID NO 5
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: T7-lang, RACE-primer

<400> SEQUENCE: 5
```

```
gtaatacgac tcactatagg gcgaattggg                                    30
```

```
<210> SEQ ID NO 6
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: M13rev; RACE-primer

<400> SEQUENCE: 6
ggaaacagct atgaccatg                                                19
```

```
<210> SEQ ID NO 7
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: PP291AOS5R; gene-specific RACE-primer

<400> SEQUENCE: 7
tcacctcatc cgatacgcta gtc                                           23
```

```
<210> SEQ ID NO 8
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Pp364AOS5R; gene-specific RACE-primer

<400> SEQUENCE: 8
gtcgatgtcg tctcaatgtt cc                                            22
```

```
<210> SEQ ID NO 9
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Pp364AOS5R2; gene-specific RACE-primer

<400> SEQUENCE: 9
ccattcgtga ttgccagaac tgc                                           23
```

```
<210> SEQ ID NO 10
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Pp291/5'-SphI; Expression primer

<400> SEQUENCE: 10
aaagcatgca tggcagtccc ttcatccaag c                                  31
```

```
<210> SEQ ID NO 11
<211> LENGTH: 45
<212> TYPE: DNA
<213> ORGANISM: Artificial Sequence
<220> FEATURE:
<221> NAME/KEY: misc_feature
```

```
<222> LOCATION: (1)..(45)
<223> OTHER INFORMATION: Pp291/3'PstI; Expression primer

<400> SEQUENCE: 11
aaactgcagt cacttttga gatcggaaaa gaaaaccttg gtcgc                45

<210> SEQ ID NO 12
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Pp364/5'BamHI; Expression primer

<400> SEQUENCE: 12
ggatcccgta cggttgtagc cagtcttggg                                30

<210> SEQ ID NO 13
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Pp364/3'HindIII; Expression primer

<400> SEQUENCE: 13
aagctttcaa tctgatcgcg gcgtcagtg                                 29
```